(12) United States Patent
Epstein

(10) Patent No.: US 10,881,537 B2
(45) Date of Patent: Jan. 5, 2021

(54) STRUCTURAL HYDROGEL POLYMER DEVICE

(71) Applicant: Scott M. Epstein, Boston, MA (US)

(72) Inventor: Scott M. Epstein, Boston, MA (US)

( * ) Notice: Subject to any disclaimer, the term of this patent is extended or adjusted under 35 U.S.C. 154(b) by 1107 days.

(21) Appl. No.: 14/881,753

(22) Filed: Oct. 13, 2015

(65) Prior Publication Data
US 2016/0166412 A1 Jun. 16, 2016

Related U.S. Application Data

(63) Continuation of application No. 13/231,752, filed on Sep. 13, 2011, now Pat. No. 9,180,028, which is a (Continued)

(51) Int. Cl.
| | |
|---|---|
| *A61F 2/82* | (2013.01) |
| *A61F 2/844* | (2013.01) |
| *A61L 29/04* | (2006.01) |
| *A61L 29/14* | (2006.01) |
| *A61L 31/04* | (2006.01) |
| *A61L 31/14* | (2006.01) |
| *A61M 25/00* | (2006.01) |

(52) U.S. Cl.
CPC .......... *A61F 2/844* (2013.01); *A61F 2/82* (2013.01); *A61L 29/041* (2013.01); *A61L 29/145* (2013.01); *A61L 31/048* (2013.01); *A61L 31/145* (2013.01); *A61M 25/0017* (2013.01); *A61M 2207/00* (2013.01)

(58) Field of Classification Search
CPC .......... A61F 2/844; A61F 2/82; A61L 29/041; A61L 29/145; A61L 31/048; A61L 31/145; A61M 25/0017
USPC ....... 264/171.26, 204, 209.1, 209.2; 623/1.1, 623/1.15, 1.22, 1.44, 1.49; 156/184, 195, 156/244.13
See application file for complete search history.

(56) References Cited

U.S. PATENT DOCUMENTS

| | | |
|---|---|---|
| 3,862,452 A | 1/1975 | Wichterle et al. |
| 3,890,683 A | 6/1975 | Vodnansky et al. |
| | (Continued) | |

FOREIGN PATENT DOCUMENTS

WO 0018446 A1 4/2000

OTHER PUBLICATIONS

W.K. Wan et al. "Optimizing the Tensile properties of Polyvinyl Alcohol Hydrogel for the Construction of a Bioprosthetic Heart Valve Stent", J Biomed Mater Res (Appl Biomater), vol. 63, pp. 854-861 (2002).

*Primary Examiner* — Michael N Orlando
*Assistant Examiner* — Elizabeth Bradford
(74) *Attorney, Agent, or Firm* — Intrinsic Law Corp.

(57) ABSTRACT

The present invention relates generally a manufacturing process which results in a completely hydrogel polymer device that maintains lumen patency which allows for numerous applications. Catheters and stents are particular examples, and their composition, mechanical characteristics, and the significantly unique ability to conduct and allow fluids to pass from one end to the other without physiological rejection, inflammation, or manifestation of complications due to implant or otherwise undesirable outcomes when used for ambulatory and or therapeutic interventions is the purpose of the invention.

30 Claims, 13 Drawing Sheets

STEP 1.0

STEP 2.0

Related U.S. Application Data continuation of application No. 11/590,219, filed on Oct. 31, 2006, now Pat. No. 8,048,350.

(60) Provisional application No. 60/731,740, filed on Oct. 31, 2005.

(56) References Cited

U.S. PATENT DOCUMENTS

| | | |
|---|---|---|
| 4,026,296 A | 5/1977 | Stoy et al. |
| 4,183,884 A | 1/1980 | Wichterle et al. |
| 4,475,972 A | 10/1984 | Wong |
| 4,762,128 A | 8/1988 | Rosenbluth |
| 4,943,618 A | 7/1990 | Stoy et al. |
| 5,149,052 A | 9/1992 | Stoy et al. |
| 5,601,881 A | 2/1997 | Grimm et al. |
| 6,039,694 A | 3/2000 | Larson et al. |
| 6,060,534 A * | 5/2000 | Ronan .................. A61L 29/145 424/422 |
| 6,200,257 B1 | 3/2001 | Winkler |
| 6,368,356 B1 | 4/2002 | Zhong et al. |
| 6,488,802 B1 | 12/2002 | Levingston et al. |
| 6,547,908 B2 | 4/2003 | Keyes et al. |
| 8,048,350 B2 | 11/2011 | Epstein |
| 2002/0143385 A1 | 10/2002 | Yang |
| 2002/0156342 A1* | 10/2002 | Burton .................. A61F 2/0027 600/29 |
| 2003/0021762 A1 | 1/2003 | Luthra et al. |
| 2003/0211130 A1 | 11/2003 | Sanders et al. |
| 2003/0222369 A1 | 12/2003 | Nicora et al. |
| 2005/0159704 A1 | 7/2005 | Scott et al. |
| 2006/0052478 A1 | 3/2006 | Madsen et al. |

\* cited by examiner

STEP 1.0

STEP 2.0

STEP (1)    STEP (2)

STRUCTURAL HYDROGEL POLYMER DEVICE

CROSS-REFERENCE TO RELATED APPLICATIONS

This application is a continuation of U.S. application Ser. No. 13/231,752, filed Sep. 13, 2011, which is a continuation of U.S. application Ser. No. 11/590,219, filed Oct. 31, 2006 and now U.S. Pat. No. 8,048,350 which claims the benefit of U.S. Provisional Application No. 60/731,740 filed on Oct. 31, 2005, the contents of each of the aforementioned applications are incorporated herein by reference.

FIELD OF INVENTION

The present invention relates generally to a manufacturing process and a resulting apparatus which results in a completely hydrogel polymer device that maintains lumen patency which allows for numerous applications, particularly, catheters and stents.

BACKGROUND OF THE INVENTION

Generally, the common approaches utilized in the art to fabricate a product from hydrolyzed PAN entail typically coagulating a single layer or heavily plasticizing a solvent based formula hydrolyzed PAN, in order that it may be molded or extruded by conventional thermoplastic extrusion or injection molding methods. Unfortunately, do to limitations, these materials and related processes are not reliable and often lead to inconsistencies in production and/or components.

As referenced in U.S. Pat. No. 6,232,406 and in fact improvements so noted in U.S. Pat. No. 4,943,618 are probably not necessary when manufacturing a product with the disclosed process. Many types of devices are available and generally well known in the art of catheter design and construction which exhibit various curved and coiled end geometrical configurations for anchorage while others rely on material and polymer characteristics to increase performance and patient comfort. It is also generally known that some devices can be particularly difficult to implant, and withdraw. Unfortunately these designs do not minimize migrations and their lubricous coatings, which will erode off, do not diminish patient comfort, and encrustation.

In a typical modality, conventional thermoplastic polyurethane Ureteral Stent or Catheter is likely to migrate due to physiological or peristaltic organ and or muscle movement. Thereafter the device may become dislodged from its location rendering it ineffective. Additionally, after a relatively short period of time urine salts for example typically adhere to the coated and uncoated devices diminishing flow, and comfort, increasing patient pain and jeopardizing device integrity. The disclosed invention will alleviate these unacceptable complications.

SUMMARY OF INVENTION

It is the object of the invention to provide a stent or catheter fabricated in a manner totally comprised of a hydrogel capable of becoming structural in its final configuration having a cross sectional area that increases with hydration, while maintaining mechanical integrity.

It is a further object of the invention to provide a catheter or stent that incorporates a manufacturing process that results in an end product that is stable, will not erode and will exhibit tensile strengths and elongations that allow use in applications where typical thermoplastic devices are currently used. Said devices immediately exhibit lubricous surface characteristics when wetted with any aqueous media and provide increased resistance to biological complications once implanted. Substantial mechanical characteristics are exhibited by a fully hydrated device, which can be loaded with colorants, radiopacifiers and fillers.

The present invention relates generally to the field of catheters used to maintain flow in the urinary system for example and in particular a configuration that maintains an atraumatic passage where the structural hydrogel composition provides comfort, placement and mechanical advantage. Hydrolyzed polyacrylicnitrile (PAN) polymers produced utilizing the present method result in a superior end product when produced with the disclosed process. Use of this method overcomes inconstancies in present formulations and devices made in accordance with the instant process yield a 100% hydrogel composition stent, catheter or hybrid version which may can be implanted with a substantially smaller diameter and then hydrated into a predictable larger, softer size within a controllable period of time. The cathether or hybrid will also be relatively rigid for ease of placement and track-ability.

The present invention relates generally a manufacturing process which results in a completely hydrogel polymer device that maintains lumen patency which allows for numerous applications. Catheters and stems are particular examples, and their composition, mechanical characteristics, and the significantly unique ability to conduct and allow fluids to pass from one end to the other without physiological rejection, inflammation, or manifestation of complications due to implant or otherwise undesirable outcomes when used for ambulatory and or therapeutic interventions is the purpose of the invention.

Accordingly, a ureteral stent is provided having anchorage that will not migrate, exhibits resistance to encrustation and facilitates ease of implant and withdrawal. In general, the placement of the structural hydrogel, ureteral stent or catheter creates in a path from which fluids can be reliably conducted from one end to the other, which requires no significant clinical follow up due to device migration, encrustation or related patient comfort issues.

BRIEF DESCRIPTION OF THE DRAWINGS

Advantages of the present invention will be apparent from the following detailed description of exemplary embodiments thereof, which description should be considered in conjunction with the accompanying drawings, in which:

FIG. 3, step (2) discloses the basic function of the process thereafter step (1) whereby concurrent layers fuse together; inherently due to for example the solvent concentration in the concurrent outer layer and effect on the inner first layer now dehydrated for proceeding with step (2). Additionally, when and where required an adhesive can be absorbed by the dehydrated layer and or preloaded into the concurrent layer which would be extremely valuable when applying the hydrgel to other dissimilar surfaces.

FIGS. 4A & B, specifically exhibit that multiple devices can be produced simultaneously whereby hydrogel in a semi-fluid form of a specific viscosity is pumped or otherwise transported thru a manifold and out an orifice of specific size, at a specific temperature and flow rate. Additionally FIGS. 4A & B show that in setting up the process configuration, mandrel size, distance form the manifold outlet and mandrel speed both in RPM and in line speed is coordinated to the aforementioned hydrogel characteristics.

DETAILED DESCRIPTION OF PREFERRED EMBODIMENTS

A Stent or catheter or composite of the structural hydrogel and a metal, plastic or other component, and process for producing the same is illustrated herein. The finished device as disclosed is comprised of 100% Hydrogel polymer which is stable and structural in its final composition, not requiring a substrate or scaffold to maintain composition or mechanical characteristics.

Figure 1:
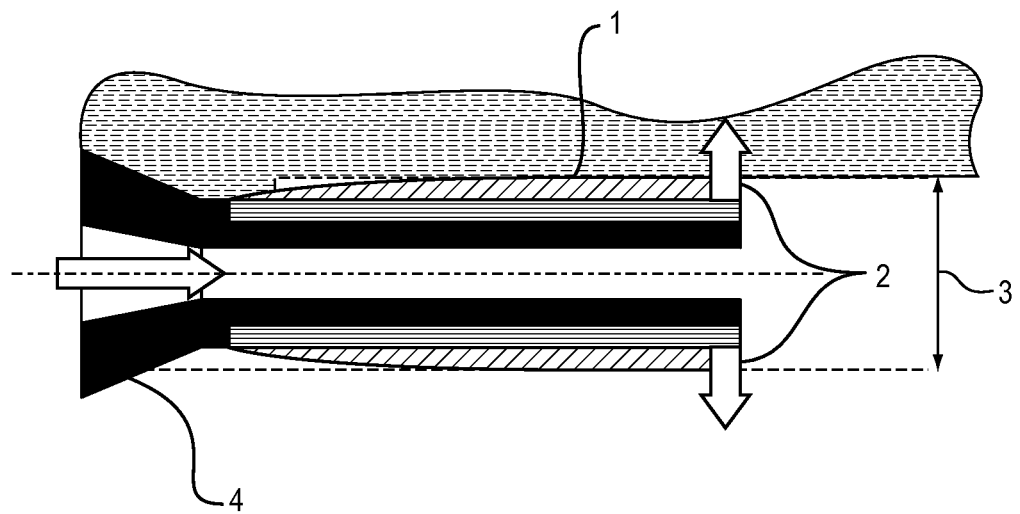
FIG. 1 is a configuration of a Stent or catheter consistent with the present invention, showing a predominant longitudinal representation and views of anchorage methods at corresponding ends. Said anchorage may be but are not limited to barbell, or trumpet profiles at one or both ends of a device.
Figure 2:
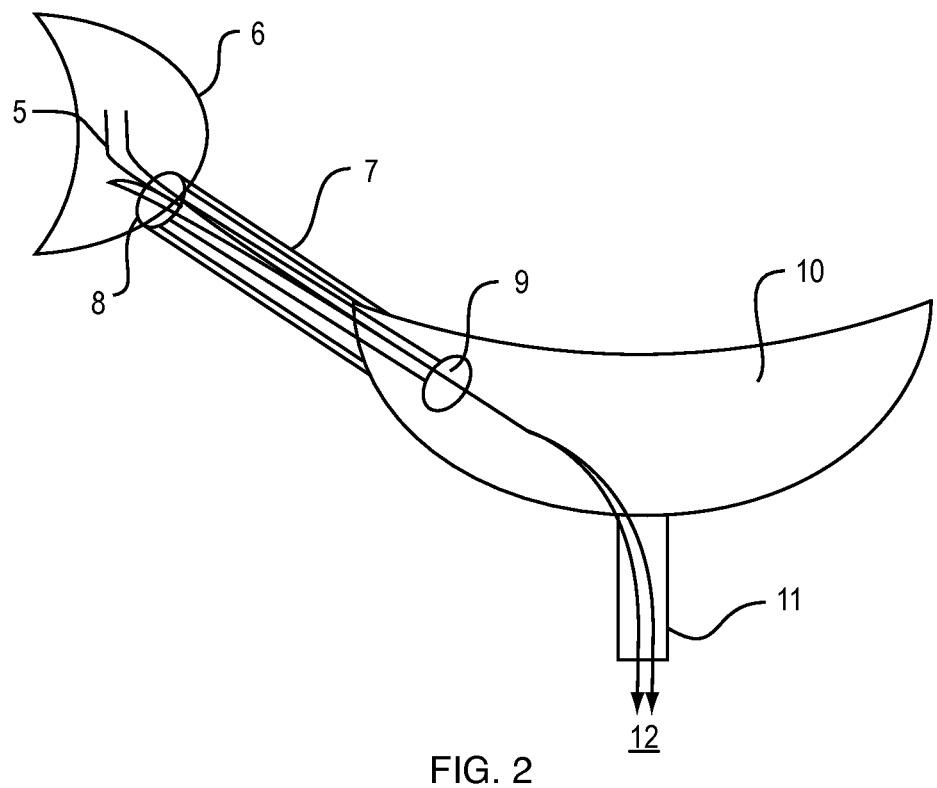
FIG. 2 is an example of the invention as applied to stenting a Ureter with predominate anchorage at distal ends in the bladder and kidney respectively maintaining placement location.

Referring now to the drawings, particularly in FIG. 1, there is generally indicated the stent of the present invention. As illustrated in FIG. 1, the body of the stent 1 is displayed, along with the uretral lumen 3 and the outward radial forces 2. The trumpet or barbell distal end for anchorage with radiopacifier fill 4 is also shown. In FIG. 2, the path urine travels through the body is shown. How the urine 5 will flow from the kidney, 6 through the anchorage in the kidney, 8 through the ureter, 7 through the anchorage of the ureter 9 and into the bladder 10. The urine will then flow 12 through the urethra 11.

Figure 3:
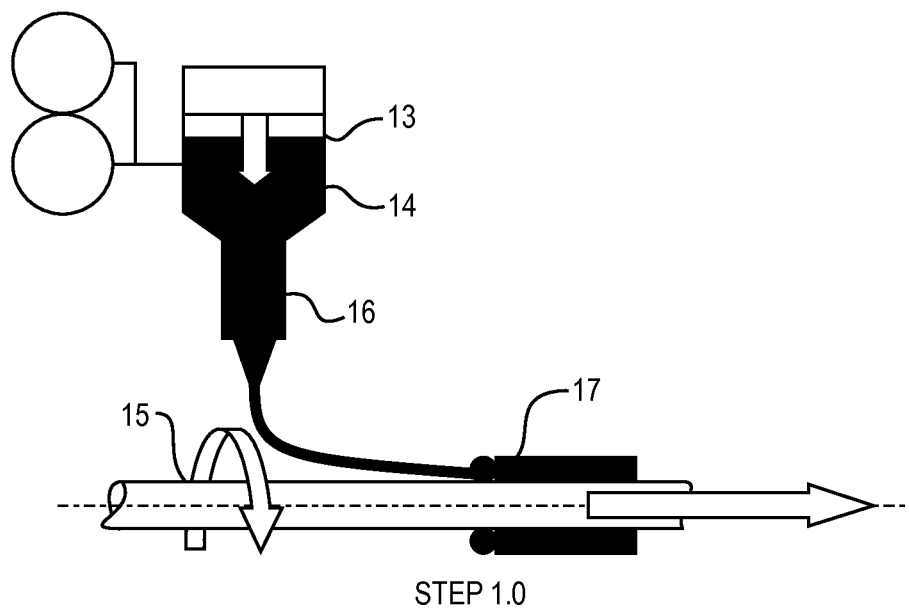
FIG. 3, step (1) discloses the basic function of the process where by after depositing the first layer, that deposition is rinsed with water essentially coagulating the hydrogel in places on the mandrel. Then the hydrogel component is rinsed and then dried either on mandrel, or can be removed from mandrel and exchanged to a smaller or larger mandrel for an additional effect. Thereafter a concurrent layer can be added.
Figure 3:
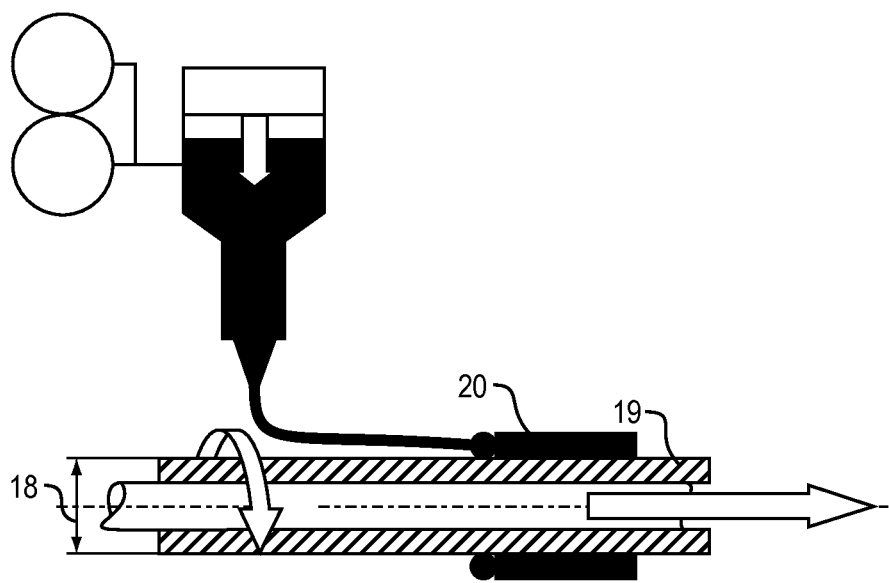

FIG. 3 displays the process of making the hydrogel stent. In step 1, the composition of the hydrogel 13 that is desired is passed through the syringe body or reservoir 14 and subsequently through a needle 16 to form the first layer 17 which will be held in place by the mandrel 15. In step 2, the process is repeated to form the second layer 20 around the first layer 19 and both held in place by the mandrel.

Figure 4A:
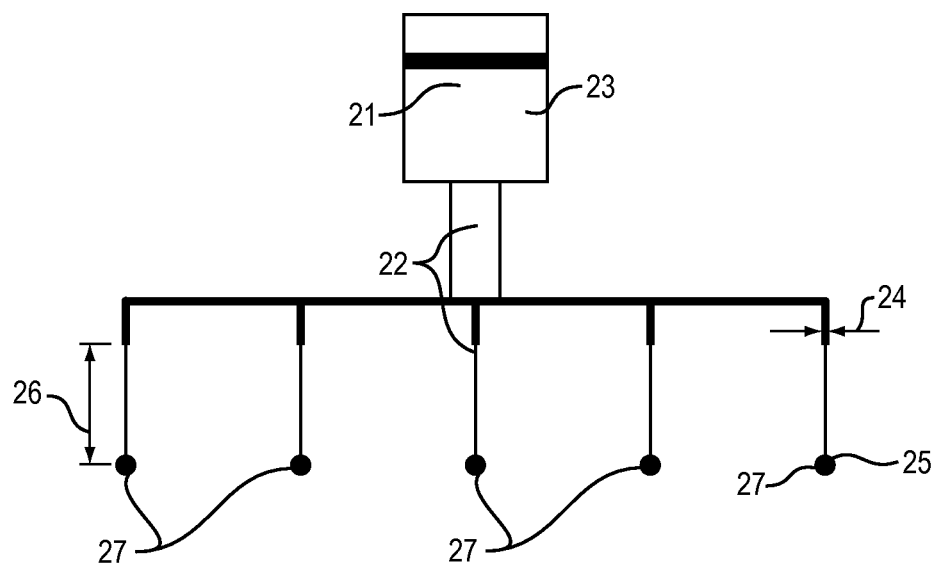
FIG. 4A, a front view, 4B, a side view, 4C a rear view & 4D, the opposing side view disclose and details the aspects of the process.
Figure 4B:
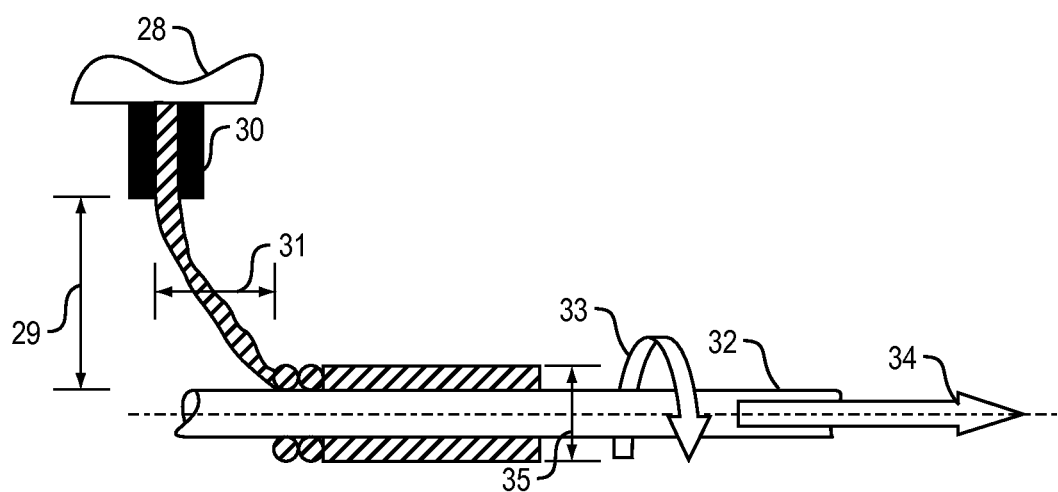
FIGS. 4C & D further identifies variations in the process whereby multiple materials can be deployed in a single process yielding one product with several materials included.
Figure 4C:
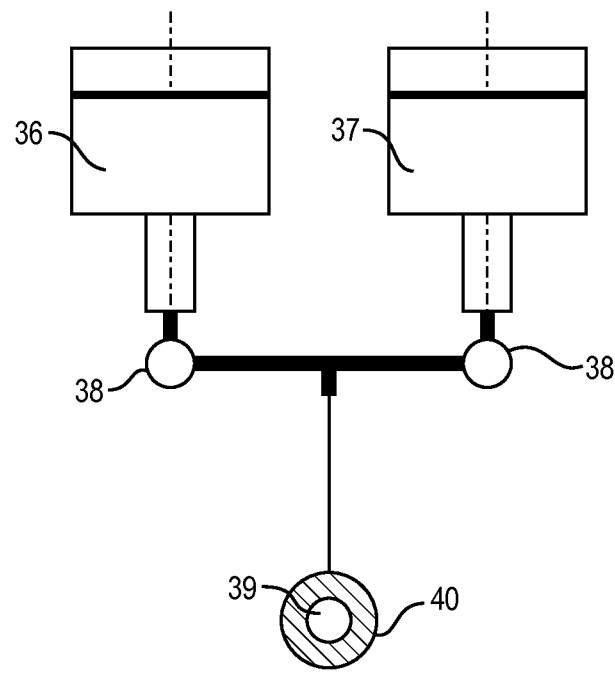
Figure 4D:
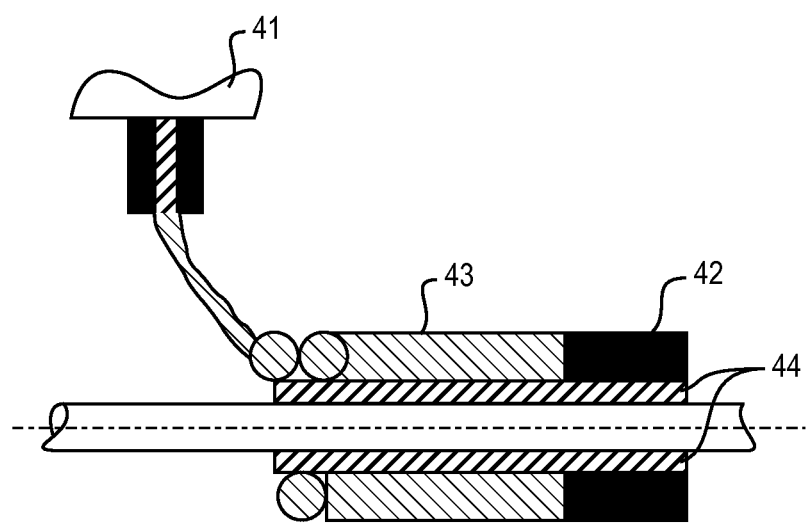

FIG. 4A the front view of the stent producing process. The adjustable process parameters of temperature, pressure and viscosity 21 and a reservoir of hydrogel in solvent solution 23 then the variable of process parameter flow rate 22. This will then go through the manifold outlet diameter 24 that allows for stents of various diameters to be created. The length of the stent can also be varied by the distance deposition filament 26. The mandrel RPM or line speed 25 can be varied and multiple stents can be received by the multiple mandrels 27. FIG. 4B shows the side view of the stent producing process. The reservoir of material 28 goes through the Outlet ID 30 which travels through a set distance 29 of the length of stent where a lead dimension is set 31. The mandrel 32 will hold a set deposition thickness 35 while rotating a set RPM 33 and coming out of the process at a certain line speed 34. FIG. 4C shows the end view of the stent producing process with reservoirs of material A 36 and material B 37. These two materials then flow through the flow direction valve 38. A mandrel 39 then holds in place where the deposition 40 will come from. FIG. 4D shows a side view from the opposite side of 4B shows the reservoir of material 41 with a material A 42 and material B 43 that make up the inner layer of the stent 44.

Figure 5A:
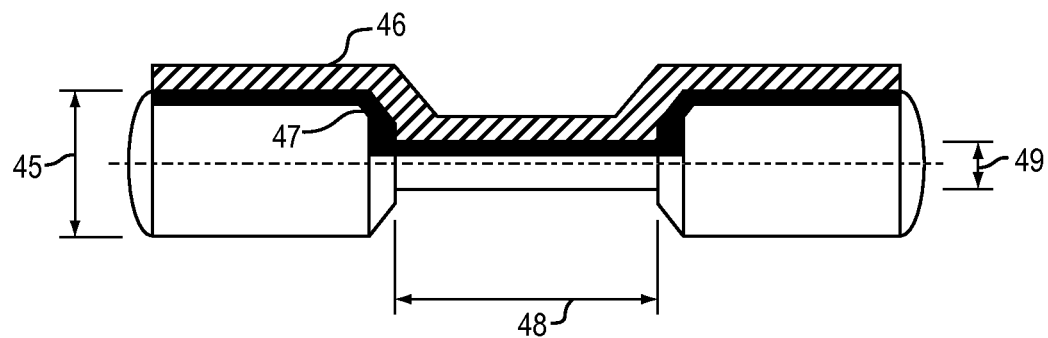
FIGS. 5A & B discloses aspects of the process whereby, mandrel design and specification can be modified in many ways contributing to end product design and performance criteria and characteristics. For example, instead of a straight uniform mandrel, FIG. 5A indicates a "barbell" shaped mandrel that allows for an as cast profile in process whereby the deposition of hydrogel conformingly coats the mandrel in process.
Figure 5B:
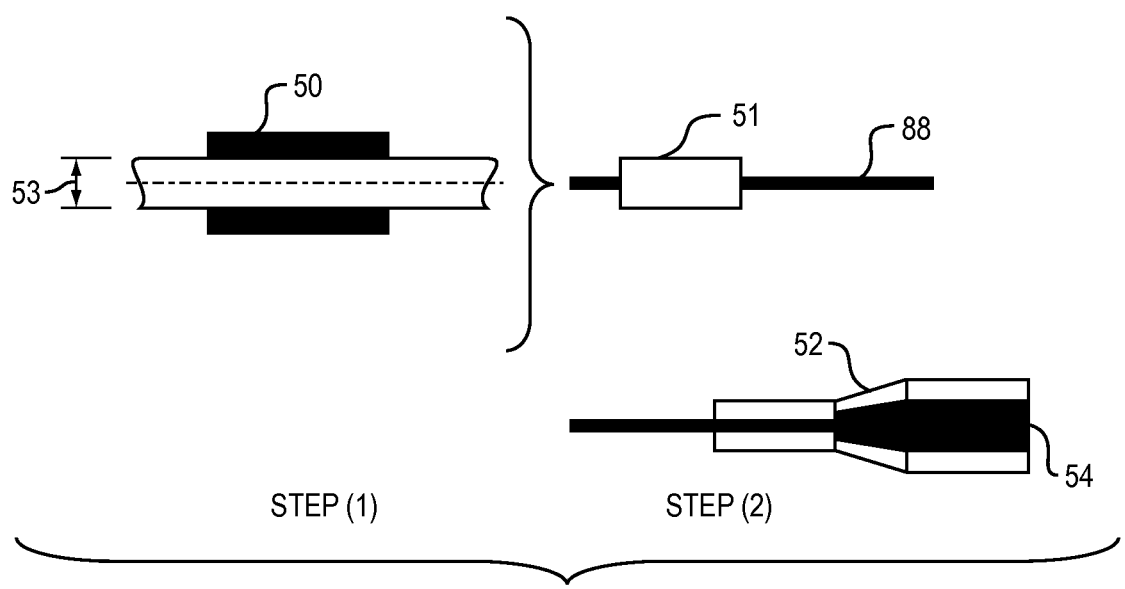
FIG. 5B discloses a method for enhancing density and or product characteristics for example by removing dehydrated deposition from mandrel in step and transferring to either a small mandrel whereby add tonal layers may exhibit greater potential compression, become denser, effect dug delivery or wicking gradients and or provide different elongation than otherwise in the same or other devices of same or similar material. Similarly, a dehydrated deposition can be transferred to a larger mandrel for further modification in process. In this manner a hydrated deposition can be dehydrated onto the larger mandrel and processed further thereafter.

FIG. 5A shows how the second layer will be attached to the first with a Mandrel dimension A 45 holding in place the subsequent outer layer 46 around the inner layer 47 with a variable mandrel length 48 and a mandrel dimension B 49. FIG. 5B shows the two step process of how the mandrel holds the structure of the stent as it comes through. In step 1, the variable mandrel diameter 53 with a deposit layer on the mandrel 50 is then dehydrated 51 onto a mandrel 88. The second step to create a smaller diameter stent is shown in step 2 with a smaller mandrel 54 with a smaller dehydrated stent 52.

Figure 6:
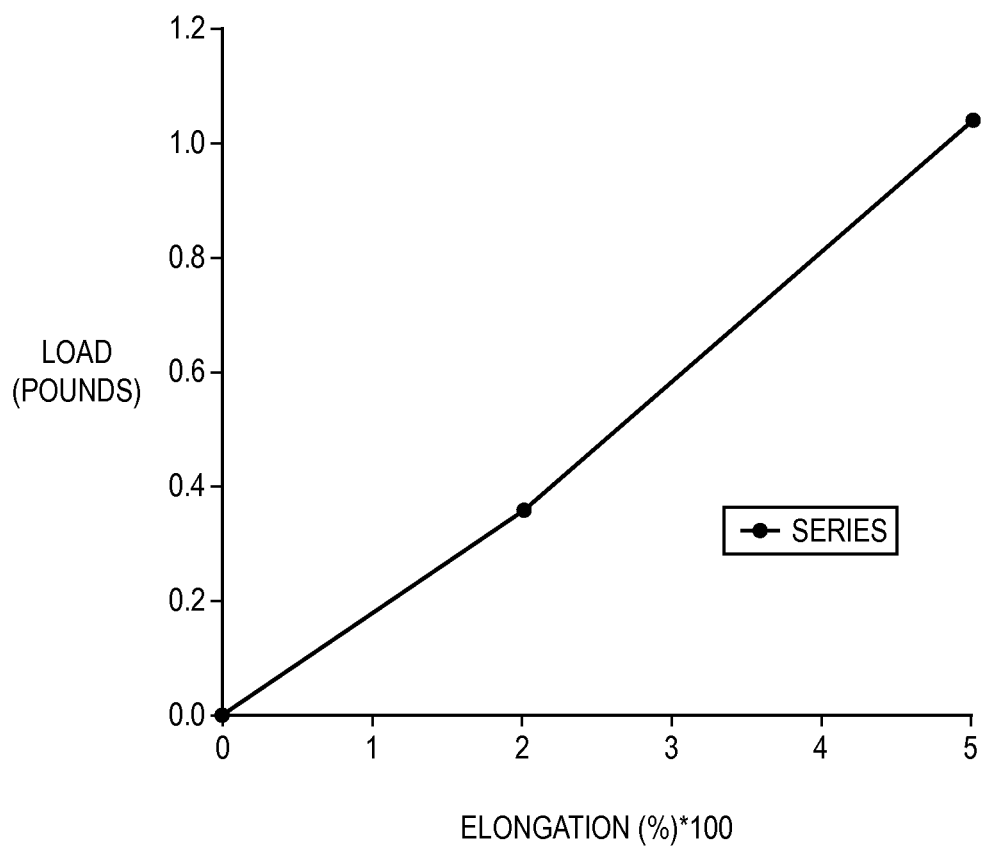
FIG. 6 is a stress/strain graph of a sample processed in accordance with the disclosed process. The low load with respect to high elongation is demonstrated.
Figure 7A:
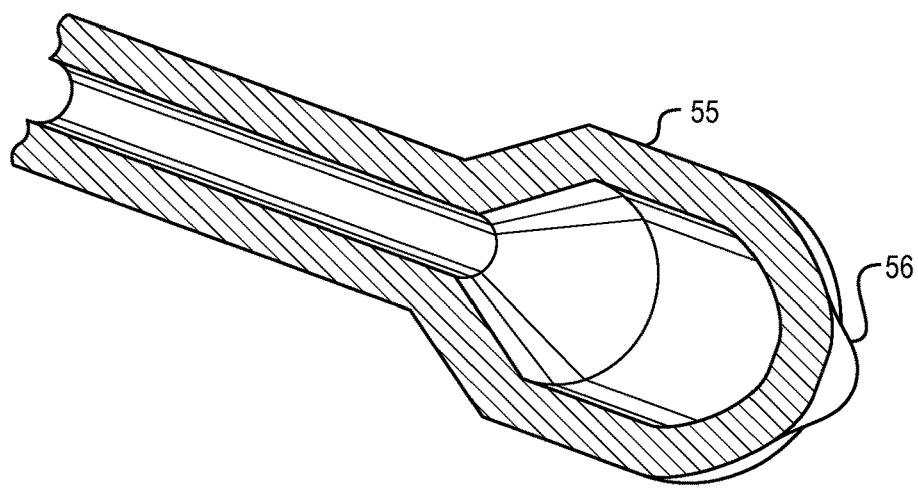
FIGS. 7A, B, C, D, E, F & G are examples of Hybrid compositions that are possible due to the disclosed process.
Figure 7B:
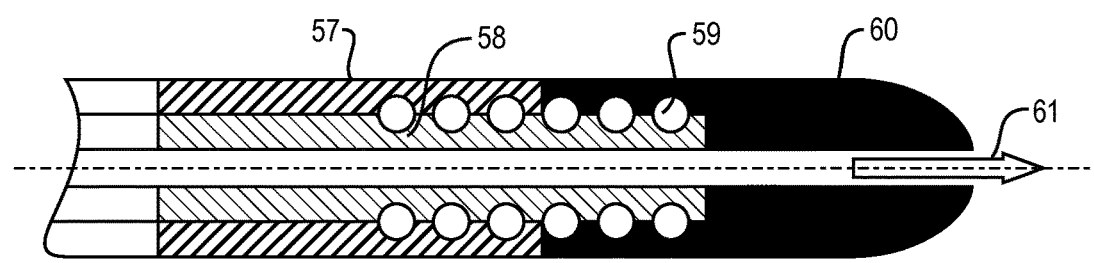
Figure 7C:
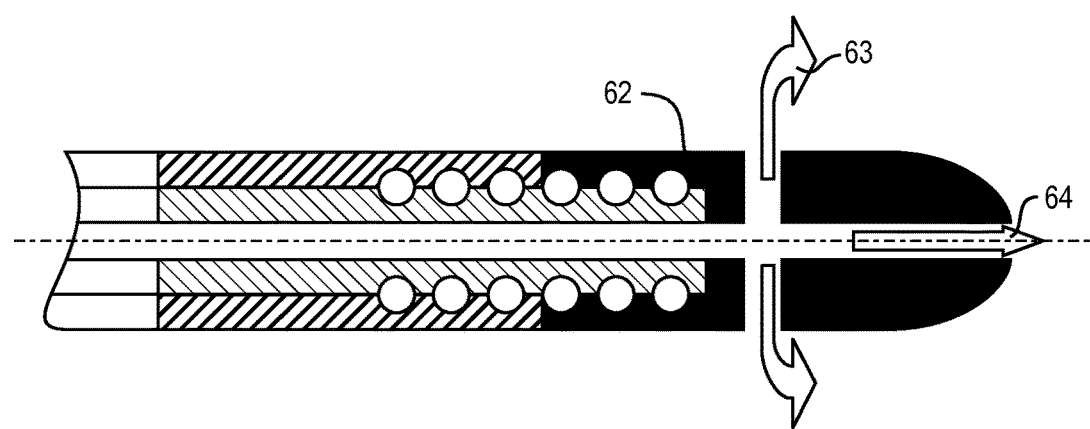

FIG. 6 is a graph depicting how much the stent can stretch based on the weight of the load applied to it. FIG. 7A shows a view of what the end of a finished structural hydrogel device 55 would look like with an embedded weave composition 56 of the final stent. FIG. 7B shows a cross section of the finished stent with an inner layer 58, an outer layer 57 a coil form 59 and a hydrogel tip 60. The flow of fluid through the stent is also shown 61. FIG. 7C shows the same cross section with a variable diameter of both the inner layer 63 and the outer layer 62 with the same outward flow 64.

Figure 7D:
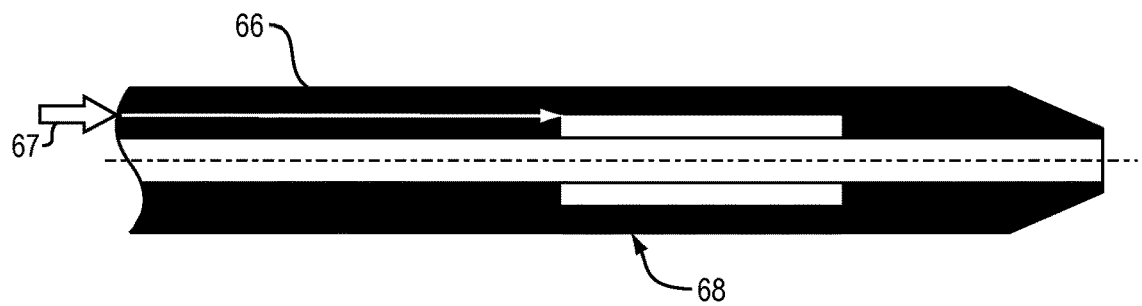

FIG. 7D shows how a catheter or stein can possibly be filled with medication that will flow into the bloodstream when the bloodstream has a lower concentration than the catheter or stent.

Figure 7E:
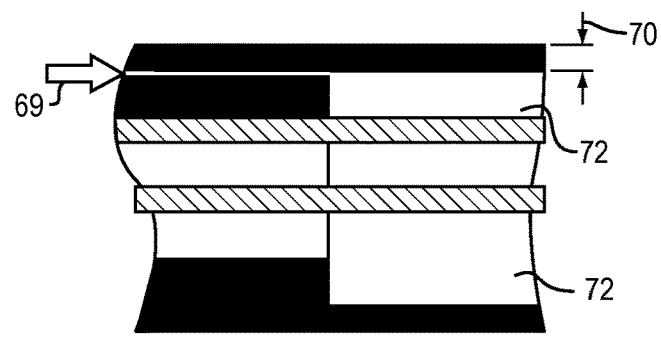
Figure 7F:
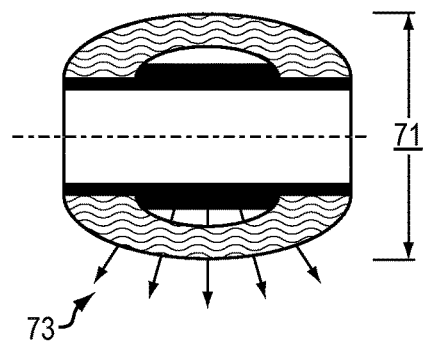
Figure 7G:
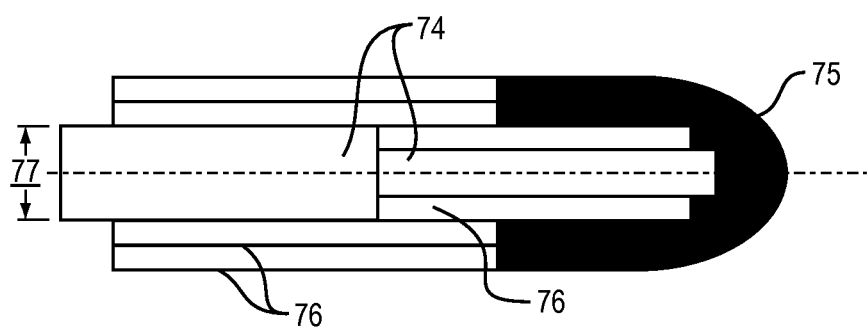
Figure 8A:
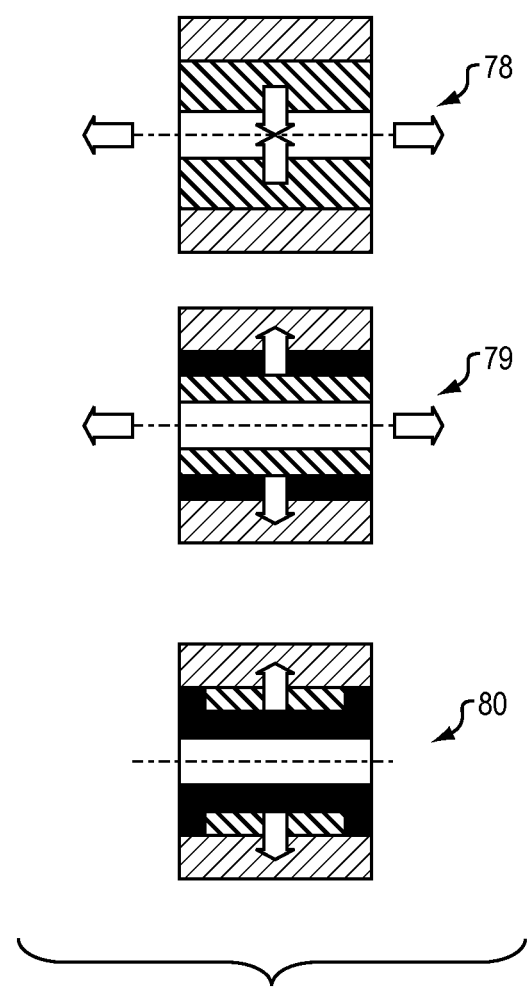
FIGS. 8A & B are examples of compositions that are possible due to the disclosed process whereby force and aqueous gradients maybe directed.

The potential inflation of the outer layer 67 of the catheter shaft 66 of a low profile integral balloon 68 is displayed. FIG. 7E shows a more detailed side view of the potential expansion for drug refilling purposes. The optional inflation 69 with a thin wall of the balloon 70 with an optional drug reservoir 72 is shown more clearly. FIG. 7F shows an end view of what the catheter or stent will look like when expanded. The increased diameter of the stent 71 with the force that is exerted outwards by the fluid flowing through 73 is displayed. FIG. 7G shows what the ends of the devices will look like if expanded. A solid core 74 with multiple layers of radiopaque filled hydrogel forming a tip 75 with the layers required by the process 76. A potential adhesive 77 could also be implemented. FIG. 8A shows three potential configurations of A 78, B, 79 and C 80.

Figure 8B:
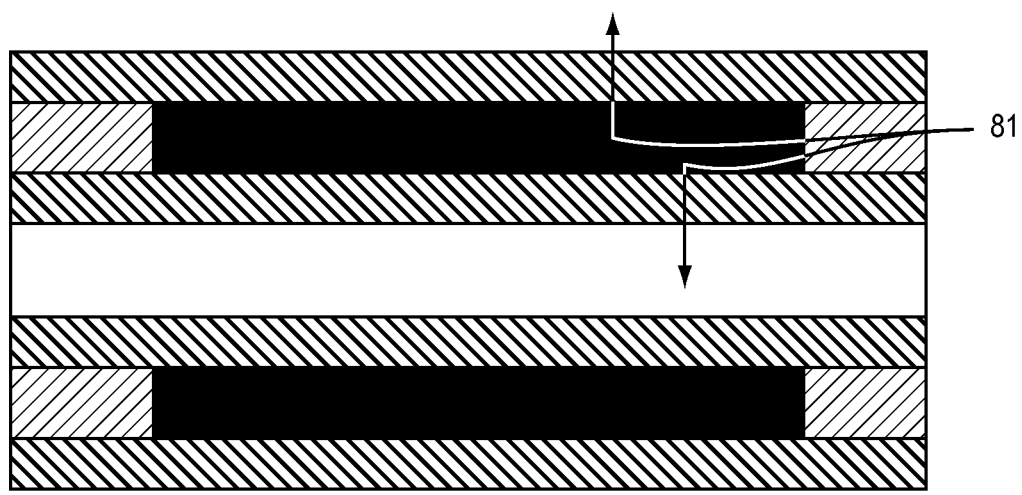
Figure 9A:
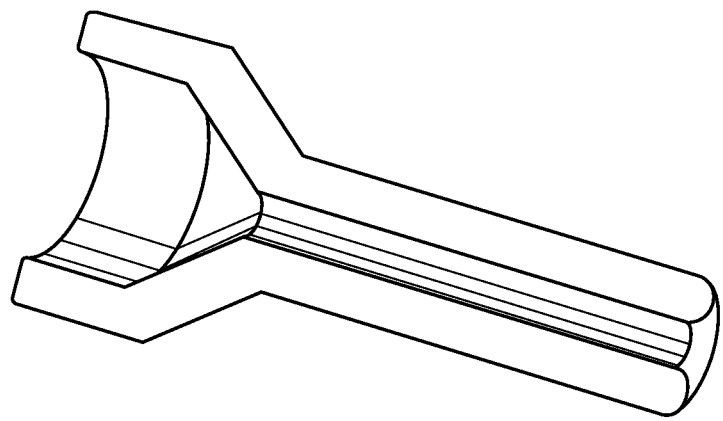
FIGS. 9A & 9B are configurations of a Stent or catheter consistent with the present invention; showing a predominant longitudinal representation and views of anchorage methods at corresponding ends. Said anchorage may be but are not limited to barbell, or trumpet profiles at one or both ends of a device.
Figure 9B:
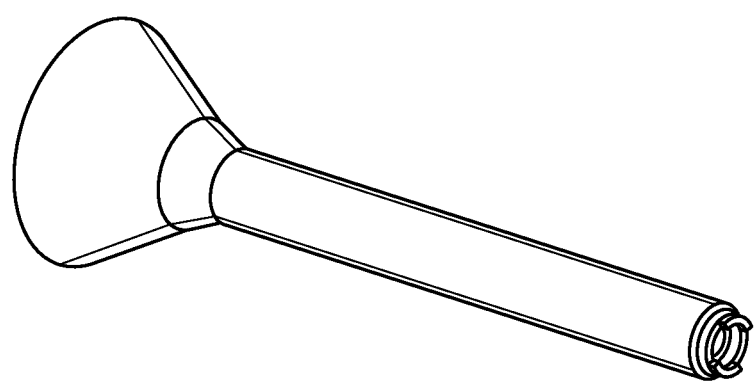

These configurations depict different potential forces that may be applied depending on the volume and amount of flow of liquid through the device. FIG. 8B shows how drugs may be delivered through diffusion 81 if that option is pursued. FIG. 9A shows an interior cross sectional view of the final device while FIG. 9B shows what the outside of the final device will look like.

Figure 10:
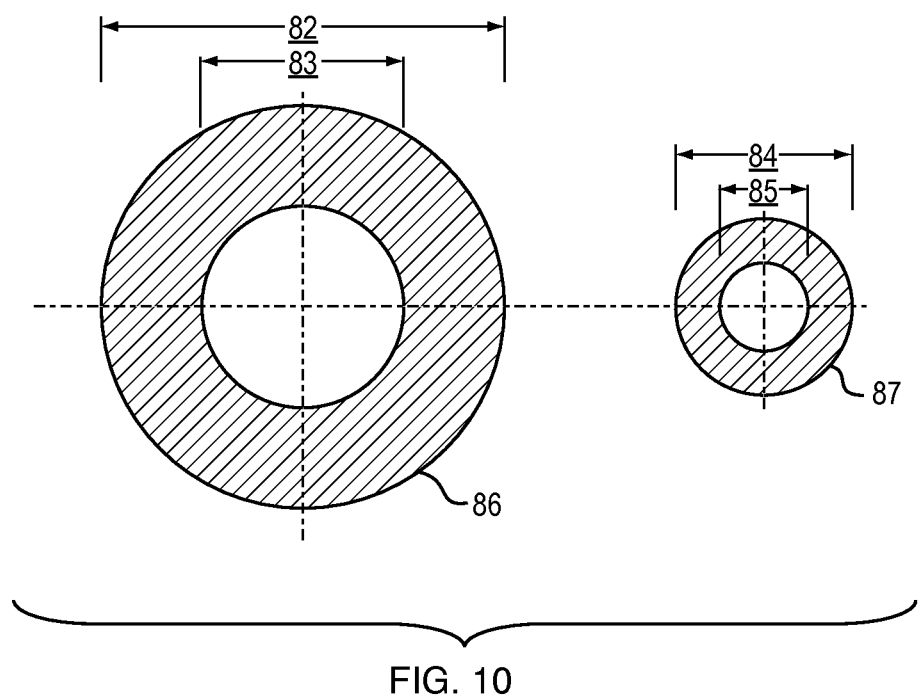
FIG. 10 is a section according to the invention illustrated to show the change in annular cross sectional area that can be expected proportional to the volume of fluid absorbed.

FIG. 10 shows the variable diameters of the outer layer with the interior diameter 83 and exterior diameter 84 when the device is fully hydrated 86. The same is shown for the inner layer with the interior diameter 85 and the exterior diameter 84 when the device is fully hydrated 87.

In the preferred embodiment, a Physician skilled in the ability can be expected to implant and retrieve a Structural Hydrogel Device in the same manner as a thermoplastic device. A Structural Hydrogel Ureteral Stent or catheter can be implanted trans-uretheraly or percutaneously from the kidney into the Ureter considerably smaller in diameter and once wetted immediately lubricous while hydrating, and increasing in corresponding volume.

This instant process ideally can be used to fabricate an entity, device or product which exhibits a reversible function, ideally infinitely where the material can be dehydrated and re-hydrated as required. In that sense, the primary mechanism of the process is that the first or inner layer material is deposited fully hydrated and then subsequently dehydrated as a part of the process, see step (1) FIG. 3, FIGS. 4A & B. Then a sequential layer is added whereby the solvent in the second layer solution that allows the hydrogel to be in a semi-liquid phase will interact with the dehydrated first or inner layer beneath and a covalent interface will be achieved, see step (2) FIG. 3, FIGS. 4A & B. This material defined as a hydrogel, is in its semi-fluid phase before solidification, and used as a raw material in the disclosed process. Furthermore different concentrations of solids or fillers in the hydrogel material can be deposited by for example controlling several reservoirs flowing into one manifold with one unique outlet, see FIGS. 4C & D.

Additionally, mandrels used for initial processing, may be removed to create additional effects. For example a larger OD mandrel will result in a thinner dehydrated wall when preparing for a concurrent layer. Similarly, a smaller OD mandrel, no mandrel or a combination of diameters could be used for additional desired effects, see FIGS. 5A & B.

Conversely, the disclosed (reversible dehydration/hydration lamination) process provides a novel advantageous alternative when designing or fabricating products made from raw materials such as hydrolyzed PAN type materials that need to exhibit excellent mechanical characteristics while maintaining low percent solids, see FIG. 6.

One of the most valuable attributes of the disclosed process allows processing from solvent-based hydrogel solutions that result in a structural hydrogel device exceeding the performance of coagulated hydrolyzed PAN products and components. Therefore the disclosed process exceeds the limitation of materials such as hydrolyzed PAN but also includes any formulation that exhibits a reversible function whereby the material can be dehydrated and re-hydrated. In that manner, the disclosed process allows the layering and or lamination of layers in accordance with the disclosed process resulting in a laminated structural hydrogel of predominately low solids and high corresponding aqueous content that will exhibit significant mechanical characteristics such that a stable product can be produced. Subsequently, this novel process allows the lamination of subsequent concurrent layers that in a final configuration provide the enhanced mechanical characteristics that result in 100% structural hydrogel products as well as hybrid versions, see FIGS. 7A, B, C, D, E, F & G.

Although one primary advantage of the disclosed process is the ability to adhere one hydrogel layer to another hydrogel layer or other surface material, and that the lamination of such layers together results in and benefit from the compression of the outer layers or at least the integration of the outer layer to the associated inner layer; one can incorporate or produce a hybrid by for example incorporating a braid or fabric between layers, see FIG. 7A.

Therefore the disclosed process results in the revolutionary never before claim of adhering one hydrogel layer to another hydrogel layer, which as disclosed is the primary influence resulting in the superior mechanical and biocompatibility performance characteristics of the as called structural hydrogel product or device.

A hybrid device for example utilizing a structural hydrogel distal tip manufactured in accordance with the disclosed process, and adhered to or processed directly onto a conventional metal, TPE/TPU device surface, such as for example a catheter where the hydrogel is not a coating but an integral component, see FIGS. 7B & C could diminish complications related to implantation.

Furthermore, a hybrid device utilizing a structural hydrogel design manufactured in accordance with the disclosed process can be engineered with different percent concentrations of solids in a specific layer, or segmented or positioned specifically along the axis of a catheter shaft for example. In this manner radiopaque media can be placed where it is desired, or a denser matrix can be produced in specific layers or segment along the axis, providing a differential gradient that would promote diffusion or conduction enhancing drainage, or providing a specific drug delivery barrier, see FIGS. 8A & B.

Otherwise, current processing of hydrolyzed PAN and alike hydrogels is limited to only primarily coagulation of freely poured or molded gel, typically into a sheet form where further processed including secondary operations that include many methods of cross-lonking such as exposure to radiation, freeze/thaw methods, and modifications to the polymer chemistry, as well as using hot acid to enhance its hydrophylicity and or primers that are required to attach coatings to an intended substrate.

This dangerous, expensive and marginally successful operation is not required with the disclosed process which produces a low solids and therefore correspondingly highly hydrophilic product.

Thermoplastic extrusion processes are possible with many hydrogel formulae, in order to make them perform like conventional TPE and TPU's. Although thermoplastic extrusion typically results in components and products that exhibit adequate mechanical characteristics, thermoplastic extrusion of for example hydrolyzed PAN does not yield a component or product that exhibits a large aqueous content compared to product manufactured from the disclosed process. Furthermore, for example extruding hydrolyzed PAN requires loading the polymer resin with large amounts of plasticizers, and when radiopacifers are added the end product contains a much higher percent of solid than exhibited by products manufactured with the disclosed process, diminishing the hydrophilicity, and bio-compatibility.

The advantages therefore are that the disclosed process which doesn't require thermoplastic processing (although it can be extruded or molded); doesn't require post processing to enhance hydrophylicity, and isn't sensitive to variations in the base polymer chemistry can be used to cost effectively derive products which will exhibit a much higher level of aqueous absorption and related bio-compatibility, which is paramount and related while exhibiting the required mechanical characteristics, which if not achieved, the device or product application wouldn't be possible.

To achieve this bio-compatibility and in accordance with the benefits of the disclosed process a catheter for example might be produced with several layers whereby the last layer is void of but all previous layers would be filled with radiopacifiers, see FIG. 9. In this manner human tissue does not come into contact with the radiopaque filler medias as would devices produced of or conventional hydrogels, TPE or TPU's.

Also drug delivery systems and attempts to force the change in volume resulting in for example predetermined radial forces can be exhibited by adding or not adding fillers or generally the specification of the percent of hydrogel solids in a given layer or layers as illustrated in FIG. 8.

What is claimed:

1. A medical device comprising:
    an inner layer including a coagulated hydrogel polymer material defining a lumen of the medical device; and
    one or more additional layers encircling the inner layer, a first of the one or more additional layers including a coagulated hydrogel polymer material fused with the underlying coagulated hydrogel polymer material of the inner layer at an interface; the interface having a structural configuration corresponding to the hydrogel polymer material of the inner layer in a dehydrated state fused to the coagulated hydrogel polymer material of the first additional layer in a solvated state;
    wherein the coagulated hydrogel polymer material of the inner layer and the coagulated hydrogel material of the first of the one or more additional layers encircling the inner layer are structurally stable so that the medical device does not require a substrate or scaffold to maintain its mechanical characteristics.

2. The medical device of claim 1, wherein the coagulated hydrogel polymer materials of the medical device resist biological infestation during use.

3. The medical device of claim 1, wherein the hydrogel polymer material of the first additional layer is configured to at least partially constrain radial expansion of the hydrogel polymer material of the inner layer upon hydration of the device thereby achieving compression of the inner layer.

4. The medical device of claim 1, wherein the medical device is configured to maintain patency of an anatomical lumen during use.

5. The medical device of claim 1, further comprising a structural element embedded in one or more hydrogel polymer materials of the device.

6. The medical device of claim 5, wherein the structural element is disposed at an interface between different layers of the device.

7. The medical device of claim 1, wherein at least one of the inner layer and the one or more additional layers comprises a radiopaque material.

8. The medical device of claim 1, wherein a hydrogel polymer material of at least one of the one or more additional layers comprises a radiopaque material, and wherein an outermost layer of the one or more additional layers does not comprise a radiopaque material.

9. The medical device of claim 1, wherein at least one of the inner layer or the one or more additional layers comprises a drug.

10. The medical device of claim 1, wherein at least a portion of at least one of the inner layer or the one or more additional layers is configured as a reservoir for a liquid.

11. The medical device of claim 1, wherein, along at least part of a length of the medical device, densities of the inner layer and the one or more additional layers are configured for preferential diffusion of liquid toward the lumen of the device when the device is in a hydrated state.

12. The medical device of claim 1, wherein, along at least a portion of a length of the medical device, densities of the inner layer and the one or more additional layers are configured for preferential diffusion of liquid away from the lumen of the device when the device is in a hydrated state.

13. The medical device of claim 1, wherein at least one of the inner layer and the one or more additional layers has a material composition that varies axially along at least a portion of the length of the device.

14. The medical device of claim 1, wherein at least one of the inner layer or the one or more additional layers has a first material composition at a first portion of a length of the device and has a second material composition different than the first material composition at a second portion of the length of the device.

15. The medical device of claim 1, wherein at least one of the inner layer or the one or more additional layers includes multiple portions along a length of the device, each portion including a hydrogel polymer material having physical or chemical properties different than those of a hydrogel polymer material of an adjacent portion.

16. The medical device of claim 1, wherein the medical device is configured for absorbing peristaltic forces to reduce the likelihood of migration when the device is in a hydrated state.

17. The medical device of claim 1, wherein at least one of the one or more additional layers includes an inflatable portion.

18. The medical device of claim 1, wherein the medical device is configured to withstand dehydration and rehydration without degradation of mechanical properties of the device.

19. The medical device of claim 1, wherein the coagulated hydrogel polymer material of the inner layer forms a lubricious surface of the lumen when the device is in a hydrated state and a hydrogel polymer material of an outermost layer of the medical device forms a lubricious outer surface of the device when the device is in a hydrated state.

20. The medical device of claim 19, wherein the hydrogel polymer material of the inner layer and a hydrogel polymer material of an outermost layer of the one or more additional layers of the medical device exhibit lubricious surface properties immediately upon wetting.

21. The medical device of claim 1, wherein the hydrogel polymer material of the inner layer has a different composition than the hydrogel polymer material of the first additional layer.

22. The medical device of claim 1, wherein the medical device is a stent or a catheter.

23. The medical device of claim 1, further comprising a hydrogel tip disposed at a first end of the medical device.

24. The medical device of claim 23, wherein the hydrogel tip comprises a radiopaque filled hydrogel.

25. The medical device of claim 23, wherein the hydrogel tip has a rounded profile.

26. The medical device of claim 9, wherein the medical device consists of the coagulated hydrogel polymer material.

27. The medical device of claim 1, wherein the coagulated hydrogel polymer material of the inner layer and the coagulated hydrogel polymer material of the first of the one or more additional layers encircling the inner layer are structural elements and the medical device does not require any other structural elements comprises:

the coagulated hydrogel polymer material of the inner layer and the coagulated hydrogel polymer material of the first of the one or more additional layers encircling the inner layer are structural elements that provide mechanical characteristics sufficient to maintain patency of the lumen of the medical device without any need for other structural elements.

28. The medical device of claim 27, wherein the coagulated hydrogel polymer material of the inner layer and the coagulated hydrogel polymer material of the first of the one or more additional layers encircling the inner layer maintain patency of the lumen of the medical device without contribution from any other structural elements.

29. The medical device of claim 1, wherein the coagulated hydrogel polymer material of the inner layer and the coagulated hydrogel polymer material of the first of the one or more additional layers encircling the inner layer are structural elements and the medical device does not require any other structural elements comprises:

the coagulated hydrogel polymer material of the inner layer and the coagulated hydrogel polymer material of the first of the one or more additional layers encircling the inner layer are structural elements that provide mechanical characteristics sufficient to maintain patency of an anatomical lumen without any need for other structural elements.

30. The medical device of claim 29, wherein the coagulated hydrogel polymer material of the inner layer and the coagulated hydrogel polymer material of the first of the one or more additional layers encircling the inner layer maintain patency of the anatomical lumen without contribution from any other structural elements.

* * * * *